United States Patent [19]

Arraudeau et al.

[11] Patent Number: 5,766,613
[45] Date of Patent: Jun. 16, 1998

[54] USE OF BENZOIC ACID DERIVATIVES TO STIMULATE THE PROCESS OF EPIDERMAL RENEWAL

[75] Inventors: Jean-Pierre Arraudeau, Paris; Lucien Aubert, Cap D'Ail, both of France

[73] Assignee: L'Oreal, Paris, France

[21] Appl. No.: 684,863

[22] Filed: Jul. 25, 1996

[30] Foreign Application Priority Data

Jul. 31, 1995 [FR] France .................................. 95 09305

[51] Int. Cl.⁶ ..................................................... A61K 7/48
[52] U.S. Cl. .......................... 424/401; 514/568; 514/844; 514/846; 514/859
[58] Field of Search .......................... 424/401; 514/568, 514/844, 846, 859

[56] References Cited

U.S. PATENT DOCUMENTS 3,161,566 12/1964 Turkewitsch .............................. 107/61

FOREIGN PATENT DOCUMENTS

WO 95/03028  2/1995  WIPO.

OTHER PUBLICATIONS

Chemical Abstracts, vol. 120, No. 3, 17 Jan. 1994. Abstract No. 24937. Yoko Koikawa et al. "Antiaging Cosmetics Containing Plant Extracts".

C. Montesions et al. "Superoxide Scavenging Properties of Phenolic Acids". *Plant Medica*, vol. 57, p. 54, 1991.

Database WPI. Week 9529. English Abstract of 95–220743. "Skin Ageing Inhibitor For External Use".

*Primary Examiner*—Jyothsan Venkat
*Attorney, Agent, or Firm*—Oblon, Spivak, McClelland, Maier & Neustadt, P.C.

[57] ABSTRACT

The present invention relates to the use of dihydroxybenzoic acid in or for the manufacture of a cosmetic or dermatological composition to stimulate the process of epidermal renewal. The invention also relates to a non-therapeutic skin treatment process for the treatment of wrinkles and/or fine lines and/or blemishes of the skin.

7 Claims, No Drawings

USE OF BENZOIC ACID DERIVATIVES TO STIMULATE THE PROCESS OF EPIDERMAL RENEWAL

BACKGROUND OF THE INVENTION

1. Field of the Invention

The invention relates to the use of dihydroxybenzoic acid in or for the manufacture of a cosmetic or dermatological composition for topical application to tho skin of the face and/or body, in order to stimulate the process of epidermal renewal and/or to combat wrinkles and/or fine lines and/or blemishes of the skin. The invention also relates to a non-therapeutic skin treatment process intended for the treatment of wrinkles and/or fine lines and/or blemishes of the skin.

2. Description of the Background

It is known to use 2,5-dihydroxybenzoic acid or gentisic acid in cosmetic compositions, in particular as a skin bleaching agent (see document JP-A-05-43446), as an agent for combating free radicals (see document C. Montesinos et al., Planta Med., 57, Supplement issue 2, 1991 page A54) and as an antioxidant (see document JP-A-01-249,885 and, JP-06-24937). It is known to use a dihydroxybenzoic acid for the removal of hardened or thickened layers of keratin constituting corns and callouses (U.S. Pat. No. 3,161,566).

It is known that substances which stimulate the process of epidermal cell renewal have beneficial effects equivalent to those obtained by epidermal "peeling" and are used to combat the main clinical signs of aging of the skin, in particular the formation of wrinkles or fine lines and the appearance of actinic blemishes. Stimulation of the process of epidermal cell renewal is associated with a clinical improvement in the quality of the skin, which becomes more radiant, less wrinkled and generally younger. It also allows an improvement in the acneic state of the skin. Examples of such substances which may be mentioned are α-hydroxy acids, β-hydroxy acids such as salicylic acid, topical retinoids, etc.

It is sought to diversify the type of product used for stimulating the process of epidermal cell renewal, and there is thus a need for other products having properties of stimulating the process of epidermal cell renewal.

SUMMARY OF THE INVENTION

The Applicant has now discovered, unexpectedly, that the topical application of a dihydroxybenzoic acid, and in particular, gentisic acid, makes it possible to stimulate the process of epidermal cell renewal and the process of epidermal repair.

DETAILED DESCRIPTION OF THE INVENTION

Thus, an object of the present invention is the use of at least one dihydroxybenzoic acid in or for the manufacture of a cosmetic or dermatological composition to stimulate the process of epidermal renewal.

The use of dihydroxybenzoic acid makes it generally possible to treat any skin imperfection, in particular blemishes, skin dyschromias, dermatitides, actinic lentigos, scars and scar pigmentations, and ichthyoses. Compared with the products known previously for stimulating the process of epidermal cell renewal, dihydroxybenzoic acids have the advantage of additionally displaying other advantageous properties, in particular anti-inflammatory properties, which makes them less irritating and thus better tolerated compounds.

Thus, another object of the invention is the use of at least one dihydroxybenzoic acid in or for the manufacture of a cosmetic or dermatological composition to combat wrinkles and/or fine lines and/or actinic blemishes and/or skin dyschromias and/or ichthyosis and/or acne.

The dihydroxybenzoic acids according to the invention are compounds having the following formula:

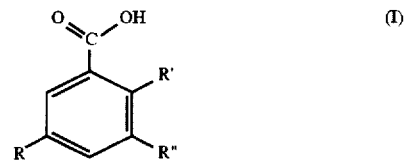

in which R, R' and R" represent, independently of each other, a hydrogen, a hydroxyl, an alkyl group or an alkoxy group, at least two of the radicals R, R' and R" representing a hydroxyl. The alkyl and alkoxy groups preferably contain from 1 to 23 carbon atoms and may also be saturated or unsaturated.

Gentisic acid and 2,3-dihydroxybenzoic acid may in particular be mentioned as dihydroxybenzoic acids of formula (I). These acids may be used as they are or in the form of natural extracts containing them. A natural extract which may be mentioned is, for example, gentian.

In the compositions according to the invention, the dihydroxybenzoic acid (or a mixture of dihydroxybenzoic acids) is used in an amount in the range from 0.1 to 30% by weight relative to the total weight of the composition, and in particular in an amount within the range from 0.2 to 10% by weight relative to the total weight of the composition.

In addition, the Applicant has observed that these compounds may be combined with other active agents known for their properties of stimulation of the process of epidermal cell renewal, for example hydroxy acids, α- or β-keto acids or retinoids. Such a combination makes it possible to reduce the active concentration of these products as a result of the addition of their effects. It is thus possible to obtain a less irritant and more effective composition.

Thus, another object of the invention is a cosmetic and/or dermatological composition, characterized in that it contains, in a physiologically acceptable medium, at least one dihydroxybenzoic acid and at least one active agent chosen from α-hydroxy acids, β-hydroxy acids, a-keto acids, β-keto acids and retinoids.

The hydroxy acids may, for example, be α-hydroxy acids or β-hydroxy acids, which may be linear, branched or cyclic, and saturated or unsaturated. The hydrogen atoms of the carbon chain may, in addition, be substituted by halo, alkyl, acyl, acyloxy, alkoxycarbonyl or alkoxy radicals having from 2 to 18 carbon atoms.

The hydroxy acids which may be used are, in particular, glycolic acid, lactic acid, malic acid, tartaric acid, citric acid and fruit acids in general, 2-hydroxyalkanoic acids, mandelic acid, salicylic acid, as well as the alkyl derivatives thereof such as 5-n-octanoylsalicyclic acid, 5-n-dodecanoylsalicyclic acid, 5-n-decanoylsalicylic acid, 5-n-octylsalicylic acid, 5-n-heptyloxysalicylic acid, 4-n-heptyloxysalicylic acid, 2-hydroxy-3-methylbenzoic acid or alkoxy derivatives thereof such as 2-hydroxy-3-methoxybenzoic acid.

The retinoids may be, in particular, retinoic acid (all-trans or 13-cis) and derivatives thereof, retinol (vitamin A) and esters thereof such as retinyl palmitate, retinyl acetate and retinyl propionate, as well as salts thereof.

By way of example, the hydroxy acids, the keto acids and the retinoids may be used in the compositions according to the invention in an amount of 0.1 to 5% by weight relative to the total weight of the composition, and preferably from 0.5 to 3%.

An in vitro test of the effectiveness of the stimulation of the process of the epidermal cell renewal produced by the compounds according to the invention was carried out on stratum corneum using salicylic acid as a reference compound. The principle of the test is based on the fact that stimulation of the process of epidermal cell renewal induces the release of corneocytes. The power of stimulation of the process of epidermal cell renewal of the test product will be greater the larger the number of corneocytes released and thus counted.

The test procedure was as follows: each product, at a concentration of 3.8 millimol in a solvent formed of PEG-400, ethanol and water (50/30/20), is tested on three samples of reconstituted stratum corneum, each sample consisting of a pastille 8 mm in diameter. The product is left in contact with the stratum corneum for 4 hours. Before counting the corneocytes detached, the tube containing the stratum corneum is shaken vigorously and a count is then taken of the corneocytes detached in Mallasez cells after 4 hours and 24 hours. The average number of corneocytes detached is calculated from the three results obtained for each product.

The same measurement is made on a control without active agent and containing only solvent, since the experiment inevitably results in the release of corneocytes, even in the absence of active agent.

The results are collated in the following table:

| Active Agent | Average number of corneocytes at T = 4 hours | Average number of corneocytes at T = 24 hours |
| --- | --- | --- |
| Solvent | 2.67 | 5.00 |
| Salicylic acid | 13.33 | 9.33 |
| Gentisic acid | 8.00 | 13.00 |
| 2,3-Dihydroxybenzoic acid | 14.64 | 18.33 |

These results show that gentisic acid and especially 2,3-dihydroxybenzoic acid have better long term properties of stimulation of the process of epidermal cell renewal than salicylic acid, in particular at T=24 hours.

A further object of the invention is a process for the cosmetic and/or dermatological treatment of wrinkles and/or fine lines and/or blemishes of the skin, which consists in applying a composition containing an effective amount of at least one dihydroxybenzoic acid to the wrinkles and/or fine lines and/or blemishes.

The composition of the invention contains a physiologically acceptable medium, and thus a cosmetically or dermatologically acceptable medium, that is to say a medium which is compatible with the skin, the nails, the mucous membranes, the tissues and the hair. The composition containing the dihydroxybenzoic acid may be applied topically to the face, the neck, the hair, the mucous membranes and the nails or any other area of body skin.

The compositions according to the invention may be in any form which is suitable for topical application, in particular in the form of aqueous, aqueous-alcoholic or oily solutions, dispersions of the lotion or serum type, aqueous, anhydrous or oily gels, emulsions of liquid or semi-liquid consistency of the milk type, obtained by dispersion of a fatty phase in an aqueous phase (O/W) or, conversely, (W/O), suspensions or emulsions of soft, semi-solid or solid consistency of the cream or gel type, microemulsions, or alternatively microcapsules, microparticles or vesicle dispersions of ionic and/or nonionic type. These compositions are prepared according to the usual methods.

The compositions may also be used on the hair in the form of the aqueous, alcoholic or aqueous-alcoholic solutions, or in the form of creams, gels, emulsions or foams or alternatively in the form of compositions for aerosols which also contain a propellant under pressure.

The amounts of the various constituents of the compositions according to the invention are those used conventionally in the fields in question.

Those compositions especially constitute protection, treatment or care creams for the face, for the hands or for the body, protection or care bodymilks, and lotions, gels or foams for care of the skin and the mucous membranes or for cleansing the skin.

The compositions may also consist of solid preparations constituting soaps or cleansing bars.

When the composition of the invention is an emulsion, the proportion of the fatty phase may be in the range from 5 to 80% by weight, and preferably from 5 to 50% by weight, relative to the total weight of the composition. The oils, the emulsifying agents and the co-emulsifying agents used in the composition in emulsion form are chosen from those used conventionally in the cosmetic or dermatological field. The emulsifying agent and optionally the co-emulsifying agent are present in the composition in a proportion within the range from 0.3 to 30% by weight, and preferably from 0.5 to 20% by weight, relative to the total weight of the composition. The emulsion may also contain lipid vesicles.

When the composition is an oily gel or solution, the amount of oil may range up to more than 90% by weight relative to the total weight of the composition.

In a known manner, the composition of the invention may also contain adjuvants which are common in the cosmetic and dermatological fields, such as hydrophilic or lipophilic gelling agents, hydrophilic or lipophilic active agents, preserving agents, antioxidants, solvents, fragrances, fillers, screening agents, odor absorbers and dyestuffs. The amounts of these various adjuvants are those used conventionally in the fields in question, and are for example 0.01 to 15% of the total weight of the composition. Depending on their nature, these adjuvants may be introduced into the fatty phase, into the aqueous phase and/or into the lipid vesicles.

Oils which can be used in the invention include mineral oils (liquid petrolatum), plant oils (avocado oil, soybean oil), animals oils, synthetic oils, silicone oils (cyclomethicone, dimethicone) and fluoro oils (perfluoropolyethers). Fatty alcohols (cetyl alcohol), fatty acids and waxes may also be used as fats.

Emulsifying agents which can be used in the invention include fatty acid esters of polyol, such as fatty esters of sorbitol, in particular polysorbates and, for example, polysorbate 60, or alternatively fatty esters of glycerol such as glyceryl monostearate.

Hydrophilic gelling agents include carboxyvinyl polymers (carbomer), acrylic copolymers such as acrylate/alkylacrylate copolymers, polyacrylamides, polysaccharides (methylcellulose), natural gums and clays. Lipophilic gelling agents include modified clays such as bentones, metal salts of fatty acids, hydrophobic silica and polyethylenes.

Hydrophilic active agents which may be used are proteins or protein hydrolysates, amino acids, polyols such as glycerol and propylene glycol, urea, allantoin, sugars and sugar derivatives, water-soluble vitamins, starch, bacterial or plant extracts, in particular Aloe vera, and moisturizing agents such as hyaluronic acid.

Lipophilic active agents which may be used are tocopherol (vitamin E) and derivatives thereof, essential fatty acids, ceramides and essential oils.

The cosmetic treatment process of the invention may be carried out in particular by applying the cosmetic or hygiene compositions as defined above, according to the usual technique for using these compositions. For example, application of creams, gels, sera, lotions or milks to the skin, the scalp and/or the mucous membranes.

Having generally described this invention, a further understanding can be obtained by reference to certain specific examples which are provided herein for purposes of illustration only and are not intended to be limiting unless otherwise specified. In these examples, the proportions indicated are percentages by weight.

EXAMPLE 1
Oil-in-water emulsion

| Oily phase: | |
| --- | --- |
| Polysorbate 60 | 2% |
| Glyceryl monostearate | 2% |
| Cetyl alcohol | 1% |
| Cyclomethicone | 2% |
| Dimethicone | 1% |
| Avocado oil | 2% |
| Soybean oil | 3% |
| Aqueous phase: | |
| Gentisic acid | 0.5% |
| Polyacrylamide | 1% |
| Glycerol | 3% |
| Methylcellulose | 0.5% |
| Preserving agents | 0.3% |
| Demineralized water | qs 100% |

To prepare the emulsion, the compounds of the oily phase on the one hand, and the compounds of the aqueous phase on the other hand, are mixed together under hot conditions (about 80° C.) and the oily phase is introduced into the aqueous phase over 15 minutes with stirring, followed by cooling to room temperature with gentle stirring. A day cream is obtained which causes stimulation of the process of epidermal cell renewal and regeneration of the skin and thus gives the skin a smoother and younger appearance than before the treatment.

EXAMPLE 2
Gel

| Gentisic acid | 1% |
| --- | --- |
| Polyacrylamide | 1.5% |
| Glycerol | 5% |
| Preserving agents | 0.3% |
| Hyaluronic acid | 0.1% |
| Propylene glycol | 2% |
| Rose water | 10% |
| Demineralized water | qs 100% |

A gel is obtained which, when applied regularly twice a week, smoothes the skin while at the same time moisturizing it without causing any irritation.

EXAMPLE 3
Lotion

| Gentisic acid | 0.3% |
| --- | --- |
| Glycolic acid | 0.3% |
| Glycerol | 1% |
| Propylene glycol | 3% |
| Hamamelis water | 5% |
| Ethyl alcohol | 5% |

-continued

| Preserving agent | 0.3% |
| --- | --- |
| Demineralized water | qs 100% |

A lotion is obtained which is suitable for treating greasy skin by stimulation of the process of epidermal cell renewal and moisturization.

The disclosure of France priority application 95-09305, filed Jul. 31, 1995, is hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for combating one or more conditions of the skin selected from the group consisting of wrinkles, fine lines, actinic blemishes, skin dyschromias, ichthyosis and acne comprising applying to the skin having said one or more conditions a composition comprising 0.1–30% by weight of at least one dihydroxybenzoic acid of the formula:

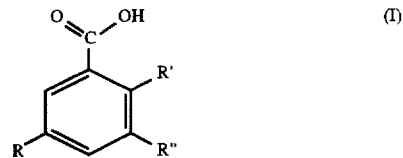

wherein R, R' and R" represent, independently, a hydrogen a hydroxyl, an alkyl group or an alkoxy group, at least two of the radicals R, R' and R" representing a hydroxyl.

2. A process according to claim 1, wherein the dihydroxybenzoic acid is selected from the group consisting of gentisic acid and 2,3-dihydroxybenzoic acid.

3. A process according to claim 1, wherein the composition also comprises at least one active agent selected from the group consisting of α-hydroxy acids, β-hydroxy acids, α-keto acids, β-keto acids and retinoids.

4. A process according to claim 1, wherein the composition also comprises at least one active agent selected from the group consisting of glycolic acid, lactic acid, malic acid, tartaric acid, citric acid, 2-hydroxyalkanoic acids, mandelic acid, salicylic acid and 5-n-octanoylsalicylic acid.

5. A process according to claim 4, wherein the active agent is present in an amount in the range from 0.1 to 5% by weight relative to the total weight of the composition.

6. A process according to claim 1, wherein the composition also contains at least one adjuvant selected from the group consisting of proteins or protein hydrolysates, amino acids, polyols, urea, sugars and sugar derivatives, vitamins, starch, plant extracts, essential fatty acids, ceramides and essential oils.

7. A process according to claim 1, wherein the composition is an aqueous, oily or aqueous-alcoholic solution, a water-in-oil emulsion, an oil-in-water emulsion, a microemulsion, an aqueous gel, an anhydrous gel, a serum or a dispersion of vesicles, of microcapsules or of microparticles.

\* \* \* \* \*

UNITED STATES PATENT AND TRADEMARK OFFICE
CERTIFICATE OF CORRECTION

PATENT NO. : 5,766,613
DATED : June 16, 1998
INVENTOR(S) : Jean-Pierre Arraudeau, et al.

It is certified that error appears in the above-identified patent and that said Letters Patent is hereby corrected as shown below:

Column 2  Line 44 "a-keto" should read --α-keto--.

Signed and Sealed this

Twenty-fifth Day of May, 1999

Attest:

Q. TODD DICKINSON

*Attesting Officer*    *Acting Commissioner of Patents and Trademarks*